(12) United States Patent
Hussey

(10) Patent No.: US 7,967,190 B2
(45) Date of Patent: Jun. 28, 2011

(54) PATIENT CARE INDICIA READER SYSTEM

(75) Inventor: Robert M. Hussey, Camillus, NY (US)

(73) Assignee: Hand Held Products, Inc., Skaneateles Falls, NY (US)

( * ) Notice: Subject to any disclaimer, the term of this patent is extended or adjusted under 35 U.S.C. 154(b) by 386 days.

(21) Appl. No.: 12/143,596

(22) Filed: Jun. 20, 2008

(65) Prior Publication Data

US 2008/0314969 A1    Dec. 25, 2008

Related U.S. Application Data

(60) Provisional application No. 60/936,396, filed on Jun. 20, 2007.

(51) Int. Cl.
    *G06F 7/10*     (2006.01)
(52) U.S. Cl. ....................................................... 235/375
(58) Field of Classification Search .................. 235/375, 235/382, 472.01–472.03
See application file for complete search history.

(56) References Cited

U.S. PATENT DOCUMENTS

| | | | |
|---|---|---|---|
| 5,825,009 A * | 10/1998 | Schmid et al. ............ | 235/462.01 |
| 6,149,063 A | 11/2000 | Reynolds et al. | |
| 6,151,581 A * | 11/2000 | Kraftson et al. ................... | 705/3 |
| 6,899,273 B2 * | 5/2005 | Hussey et al. ............ | 235/462.48 |
| 7,523,505 B2 * | 4/2009 | Menschik et al. .............. | 726/26 |
| 2008/0251579 A1 * | 10/2008 | Larsen ........................ | 235/380 |

FOREIGN PATENT DOCUMENTS

EP     1182576 A1 *    2/2002

* cited by examiner

*Primary Examiner* — Seung H Lee
(74) *Attorney, Agent, or Firm* — Hiscock & Barclay, LLP

(57) ABSTRACT

A health care service (HCS) network comprising a hand held optical reader for reading a target having information bearing indicia provided thereon and generating therefrom a decoded out indicia data message to a base unit which receives the message and transmits the message to a workstation in communication with a network server for storing the decoded out indicia data messages. The network is configured so that the server communicates non indicia data messages with the base unit which is passed to the optical reader, wherein the optical reader display is configured to display the non indicia data messages. The network is configured so that the hand held indicia reader and the base unit have a linking mode wherein a request to link is sent from the optical reader to the server through the base unit by way of wireless communication to associate the optical reader with the server.

20 Claims, 9 Drawing Sheets

PATIENT CARE INDICIA READER SYSTEM

CROSS-REFERENCE TO RELATED APPLICATIONS

This application claims the benefit of U.S. Provisional Application No. 60/936,396, filed Jun. 20, 2007, which is incorporated herein by reference in its entirety.

FIELD OF THE INVENTION

The present invention relates to indicia devices in general, and more particularly, to the linking of a wireless indicia reader with an information system.

BACKGROUND

In various environments, the use of information bearing indicia, such as bar code symbols, has become the norm for identifying products and inventory. Typically, each item is marked with information bearing indicia associated with a description of the item and other attributes (for example, price or patient identification) that are stored in a database of a host device or network system. Indicia readers are used to read the indicia and provide that reading as input information to host devices. In some cases, the data is provided to the host devices via base units, which communicate with the indicia reader. Examples of host devices include a hospital patient care system, a computer (fixed or portable), a personal digital assistant (PDA), a portable data terminal (PDT), a point of sale (POS) terminal, a transaction terminal, cash register, server, or similar device.

An advance upon the stationary presentation-type reader is the use of a mobile hand held indicia reader hardwired to a linked base unit. This configuration permits the user to manually move the hand held indicia reader into position to scan an item's indicia, rather than having to move the item into the field of view of the reader as in the stationary presentation-type reader. The scanned information from the indicia is then transmitted to the readers linked base unit via the hardwired connection between the two components. The base unit then communicates this information to the host device. Alternatively, the reader may be connected directly to the host device. Unfortunately, this approach does not eliminate the problems associated with scanning items that are out of reach of the hardwired reader and must be repositioned into the field of view of the reader so that the reader may scan the indicia.

In order to eliminate the limitations imposed by hardwiring the reader to its base unit, another proposed approach is the use of a wireless reader that may communicate wirelessly with its linked base unit. In this approach, the wireless reader is held in a base unit or docking cradle until needed to read indicia that are out of the view of a stationary presentation-type reader. The user may manually move the reader into position to scan an item's indicia as long as the reader is within a distance where it may communicate wirelessly with its linked base unit. The scanned information is then transmitted to the readers linked base unit over the wireless connection. The base unit then communicates this bar code information to the host device.

In the case of a mobile reader hardwired to its individual base unit, this link between the reader and base unit is fixed and permanent. In the case of a wireless mobile reader that communicates wirelessly with its individual base unit, this link may be made by programming the reader with information identifying the particular base unit so the reader directs its transmitted information to that base unit, or vice versa.

One prior art approach used for linking a wireless mobile reader with an individual base unit is disclosed in U.S. Pat. No. 6,149,063 to Reynolds et al. In this approach, each base unit is assigned a unique bar code symbol that is scanned by the reader to obtain information about the base unit to enable communication between the reader and the base unit.

Another prior art approach used for linking a wireless mobile reader with an individual base unit is also discussed in U.S. Pat. No. 6,149,063 to Reynolds et al. In this approach, the reader is physically inserted into a base unit. The reader and base unit then exchange information via physical mating electrical connections to enable communications between the two devices.

Efforts regarding such systems have led to continuing developments to improve their versatility, practicality and efficiency.

DETAILED DESCRIPTION

Figure 1:
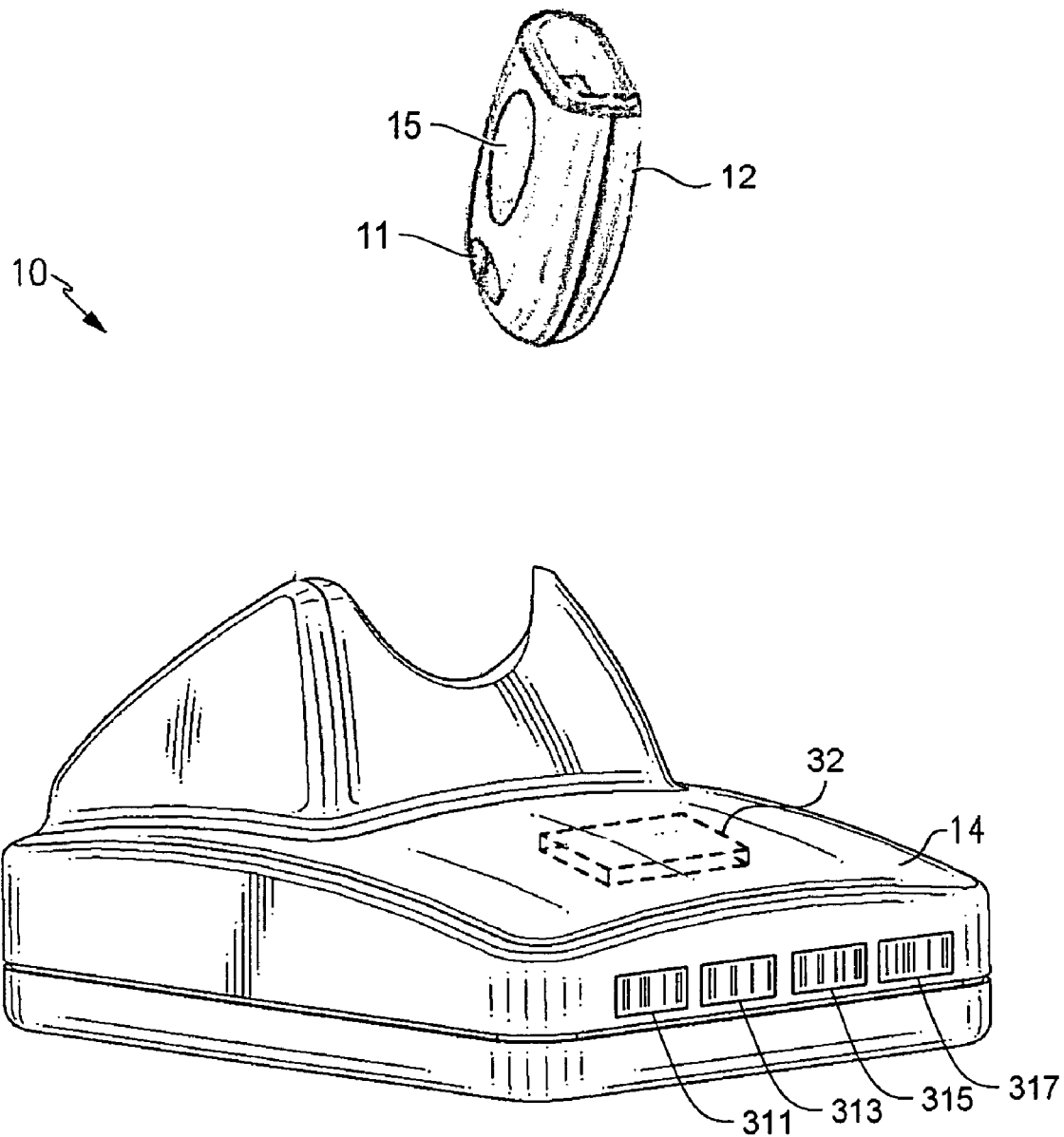
FIG. 1 illustrates an exemplary indicia reading device and base unit.

Reference will now be made in detail to the present exemplary embodiments of the invention, examples of which are illustrated in the accompanying drawings. Whenever possible, the same reference numerals will be used throughout the drawings to refer to the same or like parts for clarity.

Figure 2:
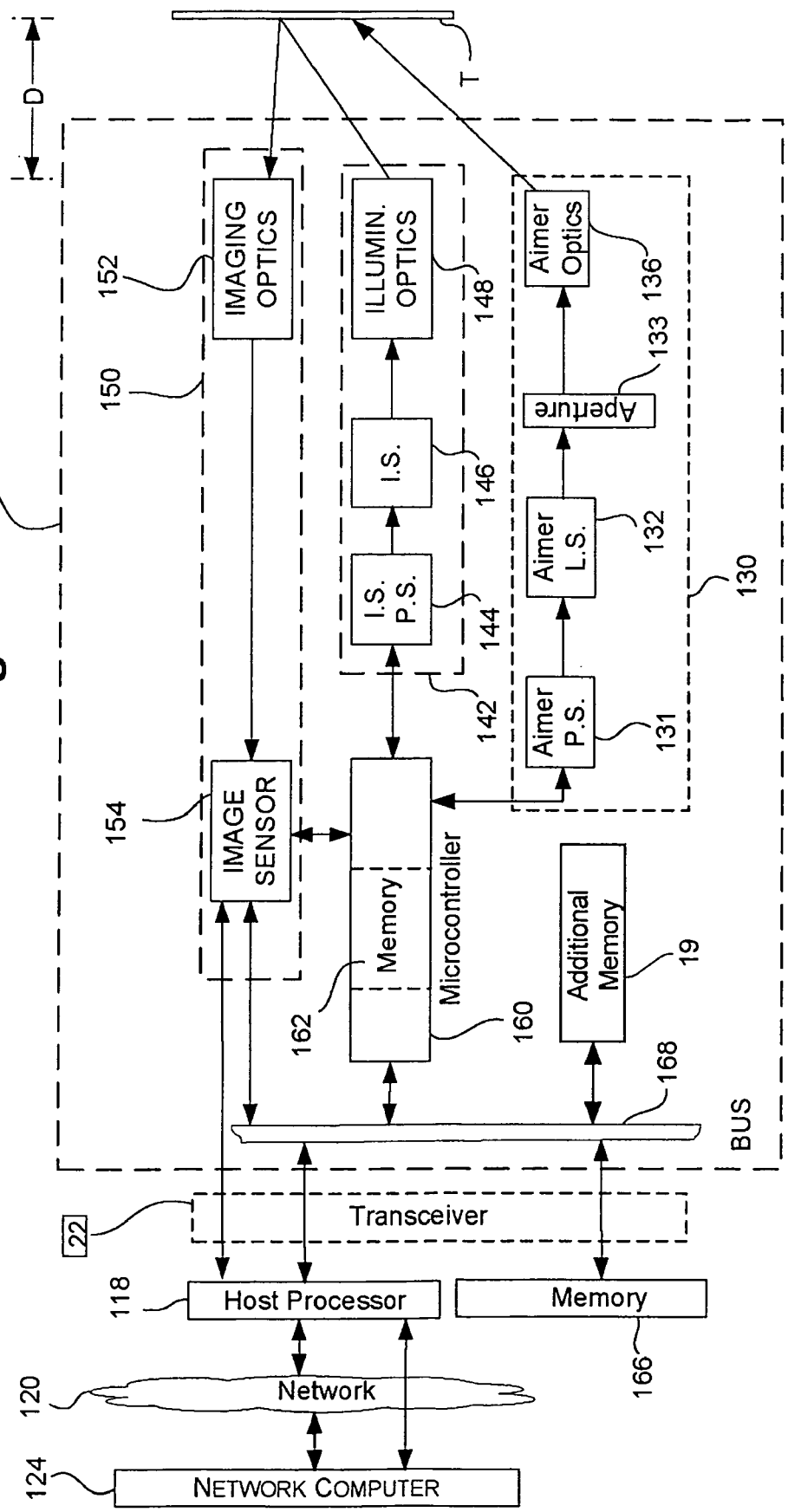
FIG. 2 is a schematic block diagram of an exemplary imaging module.
Figure 3:
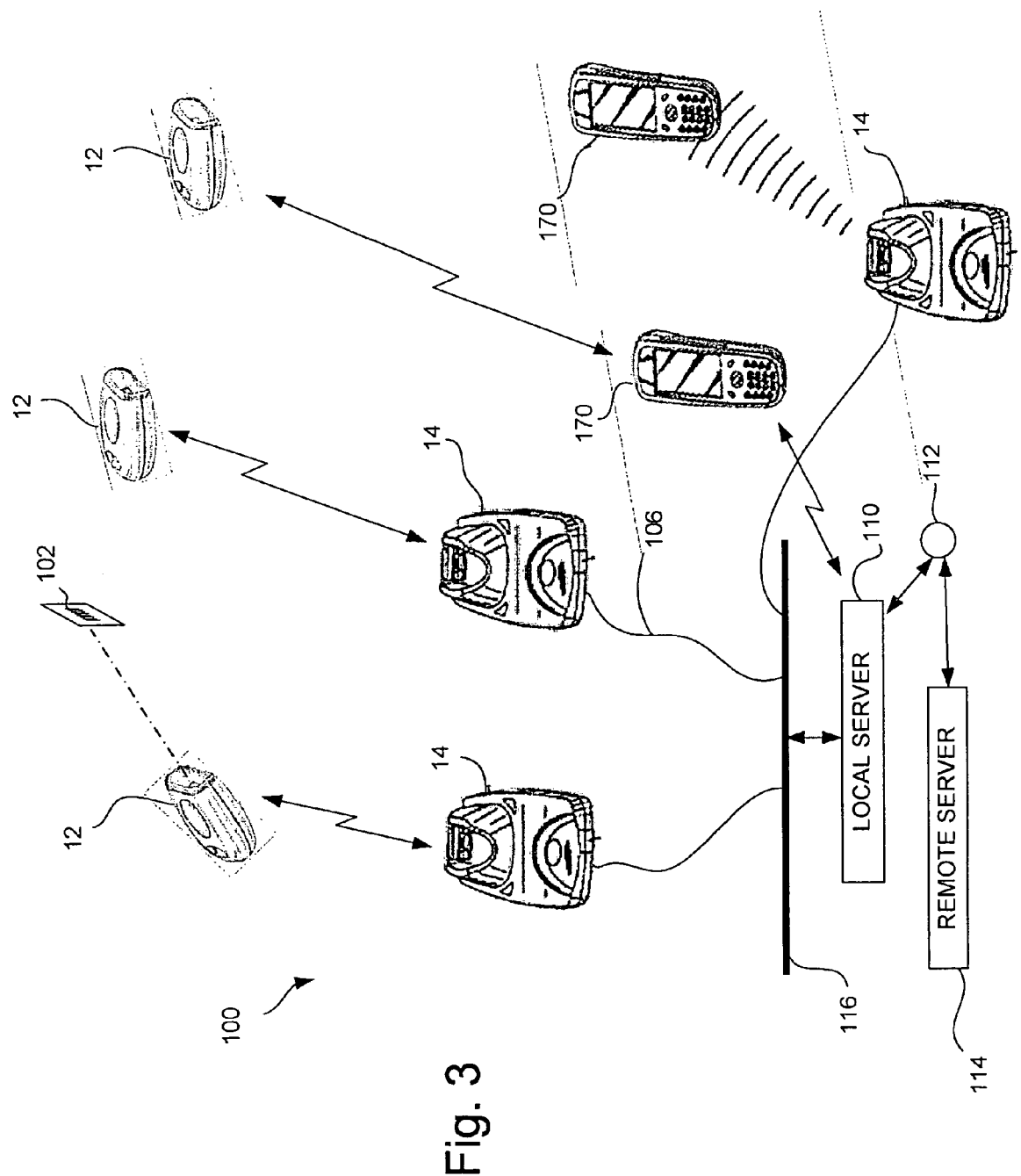
FIG. 3 is a schematic block diagram of an exemplary scanning system.

FIGS. 1 and 3 illustrate an exemplary indicia reader system 10 which includes an indicia reading device such as a reader 12 and may include a base unit 14. The reader 12 may be any device capable of reading information bearing indicia, such as bar code symbols, including linear, two dimensional, and matrix, and may be in the form of an scanner or imager or an optical reader. Examples of indicia include PDF417, MicroPDF417, MaxiCode, Data Matrix, QR Code, Aztec, Aztec Mesas, Code 49, EAN-UCC Composite, Snowflake, Dataglyphs, Code 39, Code 128, Codabar, UPC, EAN, Interleaved 2 of 5, Reduced Space Symbology, Code 93, Codablock F, and BC412, Postnet, Planet Code, British Post, Canadian Post, Japanese Post, KIX (Netherlands) Post, OCR-A, OCR-B, Code 11, UPC, EAN, MSI, Code 16K, etc. Reader 12 may include an imaging reader subassembly 13 shown in FIG. 2.

Different embodiments of the indicia reader 12 (also referred to as scanners, etc.) may typically read data represented by printed indicia, (also referred to as symbols, symbology, bar codes, etc.) but may also be configured to read or obtain information from an information bearing device, such as a card having a magnetic strip, symbol indicia such as a bar code, an RFID instrument, biogenic information such as a fingerprint, etc., or information extracted from a captured image.

Various embodiments of the reader 12 may be a hand held device, such as reader 12, personal digital assistant (PDA) 170, portable data terminal (PDT), cell phone or other platform having an image reader subassembly 13 having the capability for capturing and reading images, some of which may have symbol indicia provided therein. Personal Digital Assistants (PDAs) are typically defined as handheld devices used as a personal organizer, and having many uses such as reading information bearing indicia, calculating, use as a clock and calendar, playing computer games, accessing the Internet, sending and receiving E-mails, use as a radio or stereo, video recording, recording notes, use as an address book, and use as a spreadsheet. A plurality of buttons or keys may be used to control operation of the PDA and the imaging reader subassembly 13. A display 15 may be utilized to provide a graphical user interface (GUI).

PDAs may be equipped with the ability to query and receive and transmit data, such as firmware via a communication link, such as by radio link or wired link. Upgrading firmware from host processor to PDA (also referred to as uploading or pushing) and duplicating configuration parameters may be performed by reading specific indicia to ensure PDAs are operating at the proper revision and have the proper configuration parameters.

A PDT is typically an electronic device that is used to enter or retrieve data via wireless transmission (WLAN or WWAN) and may also serve as an indicia reader used in a stores, warehouse, hospital, or in the field to access a database from a remote location.

The PDA 170 may be a Hand Held Products Dolphin® series or the like and may include a cradle connected to a computer by a cable or wireless connection to provide two-way data communication therebetween. The computer may be replaced with a different processing device, such as a data processor, a laptop computer, a modem or other connection to a network computer server, an internet connection, or the like. The PDA may include a display and keys mounted in a case to activate and control various features on the PDA. The display may be a touch screen LCD that allows the display of various icons representative of different programs available on the PDA which may be activated by finger pressure or the touch of a stylus. The display may also be used to show indicia, graphs, tabular data, animation, or the like.

The reader 12 may be configured for hand held operation. A base unit 14 may be a docking cradle capable of charging the reader 12 or other device providing access to a host device. The housing of the reader 12 and the housing of the base unit 14 may be complementarily shaped and configured so that the reader 12 is received and supported by the base unit 14. More specifically, the lower portion of the reader 12 may be shaped and configured to be inserted into a complementarily sized socket of the base unit 14, which may then support and hold the reader 12. For example, the housing of the reader 12 may be constructed so as to ensure that it forms a friction fit connection with the base unit 14 when inserted into the socket.

Reader 12 may have a number of subsystems including an imaging reader subassembly 13 provided within a head portion or housing of reader 12 and a transceiver 31. A trigger 11 may be used for controlling full or partial operation of the reader 12.

Referring to FIG. 2, imaging reader subassembly 13 may have an aiming pattern generator 130, an illumination generator 142, an imaging system 150 and a microcontroller 160.

An exemplary aiming pattern generator 130 may be adapted to generate an aiming pattern for assisting an operator to align target T coincident with the field of view of an imaging system 150. Aiming pattern generator 130 may include a power supply 131, light source 132, aperture 133 and optics 136 to create an aiming light pattern projected on or near the target which spans a portion of the receive imaging system 150 optical system 152 operational field of view with the intent of assisting the operator to properly aim the reader at the target T indicia that is to be read. A number of representative generated aiming patterns are possible and not limited to any particular pattern or type of pattern, such as any combination of rectilinear, linear, circular, elliptical, etc. figures, whether continuous or discontinuous, i.e., defined by sets of discrete dots, dashes and the like.

Generally, the aiming light source(s) 132 may comprise any light source to provide a desired illumination pattern at the target and may be one or more LEDs 134, such as part number NSPG300A made by Nichia Corporation.

The light beam from the LEDs 132 may be directed towards an aperture 133 located in close proximity to the LEDs. An image of this back illuminated aperture 133 may then be projected out towards the target location with aimer optics 136, such as a lens. The lens may be a spherically symmetric lens, an aspheric lens, a cylindrical lens or an anamorphic lens with two different radii of curvature on their orthogonal lens axis.

Alternately, the aimer pattern generator may be a laser pattern generator. The light sources 132 may also be comprised of one or more laser diodes such as those available from Rohm. In this case a laser collimation lens (not shown) will focus the laser light to a spot generally forward of the reader and approximately at the plane of the target T. This beam may then be imaged through a diffractive interference pattern generating element, such as a holographic element fabricated with a desired pattern. Examples of these types of elements may be available for example, from Digital Optics Corp. of Charlotte, N.C. among others. Elements of these types are described in U.S. Pat. No. 4,895,790 (Swanson); U.S. Pat. No. 5,170,269 (Lin et al) and U.S. Pat. No. 5,202,775 (Feldman et al), which are hereby incorporated herein by reference.

Image reader subassembly 13 may include an illumination assembly 142 for illuminating target area T. Illumination assembly 142 may also include one or more power supplies 144, illumination source(s) 146 and illumination optics 148.

Illumination and aiming light sources with different colors may be employed. For example, in one such embodiment the illumination source(s) 146 may include white and red LEDs, red and green LEDs, white, red, and green LEDs, or some other combination chosen in response to, for example, the color of the symbols most commonly imaged by the image reader. Different colored LEDs may be each alternatively pulsed at a level in accordance with an overall power budget.

Image sensor 154 may be a two dimensional array of pixels adapted to operate in a global shutter or full frame operating mode which is a color or monochrome 2D CCD, CMOS, NMOS, PMOS, CID, CMD, etc. solid state image sensor. This sensor contains an array of light sensitive photodiodes (or pixels) that convert incident light energy into electric charge. Solid state image sensors allow regions of a full frame of image data to be addressed. An exemplary CMOS sensor is model number MT9V022 from Micron Technology Inc.

Further description of image sensors is provided in commonly owned U.S. patent application Ser. No. 11/077,995 entitled "BAR CODE READING DEVICE WITH GLOBAL ELECTRONIC SHUTTER CONTROL" filed on Mar. 11, 2005, which is hereby incorporated herein by reference in its entirety.

In a full frame (or global) shutter operating mode, the entire imager is reset before integration to remove any residual signal in the photodiodes. The photodiodes (pixels) then accumulate charge for some period of time (exposure period), with the light collection starting and ending at about the same time for all pixels. At the end of the integration period (time during which light is collected), all charges are simultaneously transferred to light shielded areas of the sensor. The light shield prevents further accumulation of charge during the readout process. The signals are then shifted out of the light shielded areas of the sensor and read out.

Features and advantages associated with incorporating a color image sensor in an imaging device, and other control features which may be incorporated in a control circuit are discussed in greater detail in U.S. Pat. No. 6,832,725 entitled "An Optical Reader Having a Color Imager" incorporated herein by reference. It is to be noted that the image sensor 154 may read images with illumination from a source other than illumination generator 142, such as from a source located remote from the reader.

The output of the image sensor may be processed in a microcontroller 160 utilizing one or more functions or algorithms to condition the signal appropriately for use in further processing downstream, including being digitized to provide a digitized image of target T.

Microcontroller 160 may perform a number of functions such as controlling the amount of illumination provided by illumination source 146 by controlling the output power provided by illumination source power supply 144. Microcontroller 160 may also control other functions and devices. An exemplary microcontroller 160 is a CY8C24223A made by Cypress Semiconductor Corporation, which is a mixed-signal array with on-chip controller devices designed to replace multiple traditional MCU-based system components with one single-chip programmable device. It may include configurable blocks of analog and digital logic, as well as programmable interconnects. Microcontroller 160 may include a predetermined amount of memory 162 for storing data. Another memory 19 connected to the bus 168 may store data that is applicable to the specific person carrying and using the reader. Such data may include tasks that need to be completed during one work day, information about patients under the care of a nurse using the reader 12, etc. The data may also be files or reference information which the person using the reader 12 would like to have readily available. In addition, the data could be one or more pictures that may have been taken by a camera in the reader.

The components in reader 112 may be connected by one or more buses 168 or data lines, such as an Inter-IC bus such as an I²C bus, which is a control bus that provides a communications link between integrated circuits in a system. This bus may connect to a host computer in relatively close proximity, on or off the same printed circuit board as used by the imaging device. I²C is a two-wire serial bus with a software-defined protocol and may be used to link such diverse components as the image sensor 154, temperature sensors, voltage level translators, EEPROMs, general-purpose I/O, A/D and D/A converters, CODECs, and microprocessors/microcontrollers.

An exemplary imaging system may include a one or more readers 12 in communication with a host processor 118. This host processor may be in communication with a network 120 which may be connected to one or more network computers 124.

The functional operation of the host processor 118 involves the performance of a number of related steps, the particulars of which may be determined by or based upon certain parameters stored in memory 166 which may be any one of a number of memory types such as RAM, ROM, EEPROM, etc. In addition some memory functions may be stored in memory 162 provided as part of the microcontroller 160. One of the functions of the host processor 118 may be to decode machine readable symbology provided within the target or captured image.

Decoding is a term used to describe the interpretation of a machine readable code contained in an image projected on the image sensor 154. The code has data or information encoded therein. Information respecting various reference decode algorithms is available from various published standards, such as by the International Standards Organization ("ISO").

Operation of the decoding, which may be executed in a user or factory selectable relationship to a scanning routine, may be governed by parameters which are enabled for processing as a part of an autodiscrimination process, whether decoding is to be continuous or discontinuous, etc. Permitted combinations of scanning and decoding parameters together define the scanning-decoding relationships or modes which the reader will use. In the continuous mode (also referred to as continuous scanning mode, continuous streaming mode, streaming mode, fly-by scanning mode, on the fly scanning mode or presentation mode) the reader is held in a stationary manner and targets (such as symbols located on packages) are passed by the reader 12. In the continuous mode, the reader takes continuous image exposures seriatim and continuously decodes or attempts to decode some or all of these images. In the continuous mode exposure times and decoding times may be limited.

Discontinuous or manual mode is a mode wherein scanning and/or decoding stops or is interrupted and initiated with an actuation event, such as depressing the trigger 11, to restart. An exemplary utilization of the reader in discontinuous mode is via hand held operation. While triggered, the image reader may expose images continuously and decode images continuously. Decoding stops once the image reader is no longer triggered. Exposing of images however, may continue. In the discontinuous mode, the exposure time, decoding time out limits and decoding aggressiveness may be increased more than those set for continuous mode. The discontinuous mode is typically initiated because the operator knows a symbol is present. The decoder therefore may forego making a determination of the presence of a symbol because a symbol is presumed to be in the field of view. Discontinuous mode may provide longer range scanning than the continuous mode.

Switching between continuous and discontinuous modes may be accomplished by use of the trigger 11 located on the reader. For example, when the trigger is depressed by an operator the reader may operate in a discontinuous mode and when the trigger is released the reader may switch to continuous mode after a predetermined period of time. A scanning subroutine may specify an address buffer space or spaces in which scan data is stored and whether scanning is to be continuous or discontinuous.

Another example of switching between continuous and discontinuous modes may be accomplished by symbology wherein switching between the modes depends on the type of symbology detected. The reader may stop attempting to decode a symbol after a predetermined time limit. The reader may limit the type of symbols to decode when in the continuous mode.

The aiming pattern generator may be programmed to operate in either continuous or discontinuous modes.

In the continuous mode, the present device may be configured to automatically switch to a reduced power state if no symbol has been sensed for a period of time. Upon sensing of a symbol the reader may then automatically switch back to the higher power state continuous mode. In this reduced power state the reader may change from having the aimer and/or illumination light sources on for every scan to having either/or on for only some of the scans (e.g. every 2 or 3 or less scans). In this manner the system may still be in a position to sense the presence of a symbol, but will draw less current and also generate less internal heating. After sensing a symbol, the image reader may utilize aiming/illumination for every scan until another period of inactivity is sensed.

Mode changes may be accomplished by the host computer in response to an appropriate signal over either a direct connection or wireless connection to the reader.

Another example of switching between modes may be accomplished by use of a trigger 11 located on the reader 12. For example, an operator may want to switch a reader's operation between two different modes, such as picture taking vs. data capture or reading only Aztec symbols vs. other symbologies or switching between continuous and discontinuous modes of operation. Switching between modes may be accomplished by detection of quick double-clicks of the trigger 11 and use detection of a quick double-click to toggle the reader in some way between different configurations and/or modes of operation. Additionally, which configuration/mode is active may be signaled back to the operator through a visual indicator (such as an LED) or an audible indicator, such as a beeper tone. The visual indication may be through different colors or patterns of blinking. The audible indicator may indicate through a beeping pattern or tone.

Different reader configurations or modes may be defined via menuing, with the trigger toggling action actually stepping through a sequence of compounded menu commands. Additionally, the time within which two clicks are considered a double-click may be predetermined and adjusted, such as by a menu.

In exemplary configurations considered herein the aimer light sources 132 are not operated during the exposure period of the image sensor and therefore the aimers do not necessarily contribute a specular reflection component derived from the Region of Interest (ROI). However the aimer in other configurations may also become a source of specular reflection.

In an exemplary embodiment, a captured image may be exported for further processing, such as indicia decoding, form recognition, image processing, optical character recognition (OCR), machine vision processing, object dimensioning, object angular subtense, coloration, object volume measurement, relative position in depth of field, motion tracking, pattern recognition, object brightness measurement, object recognition, facial or other feature recognition, spectral comparison, radiometric emmissivity, photometric emmissivity, temperature measurement, distance measurement, object proximity, etc.

In an exemplary embodiment, a captured image such exemplary further processing may be performed locally by the microcontroller 160 located within the reader housing.

Figure 4:
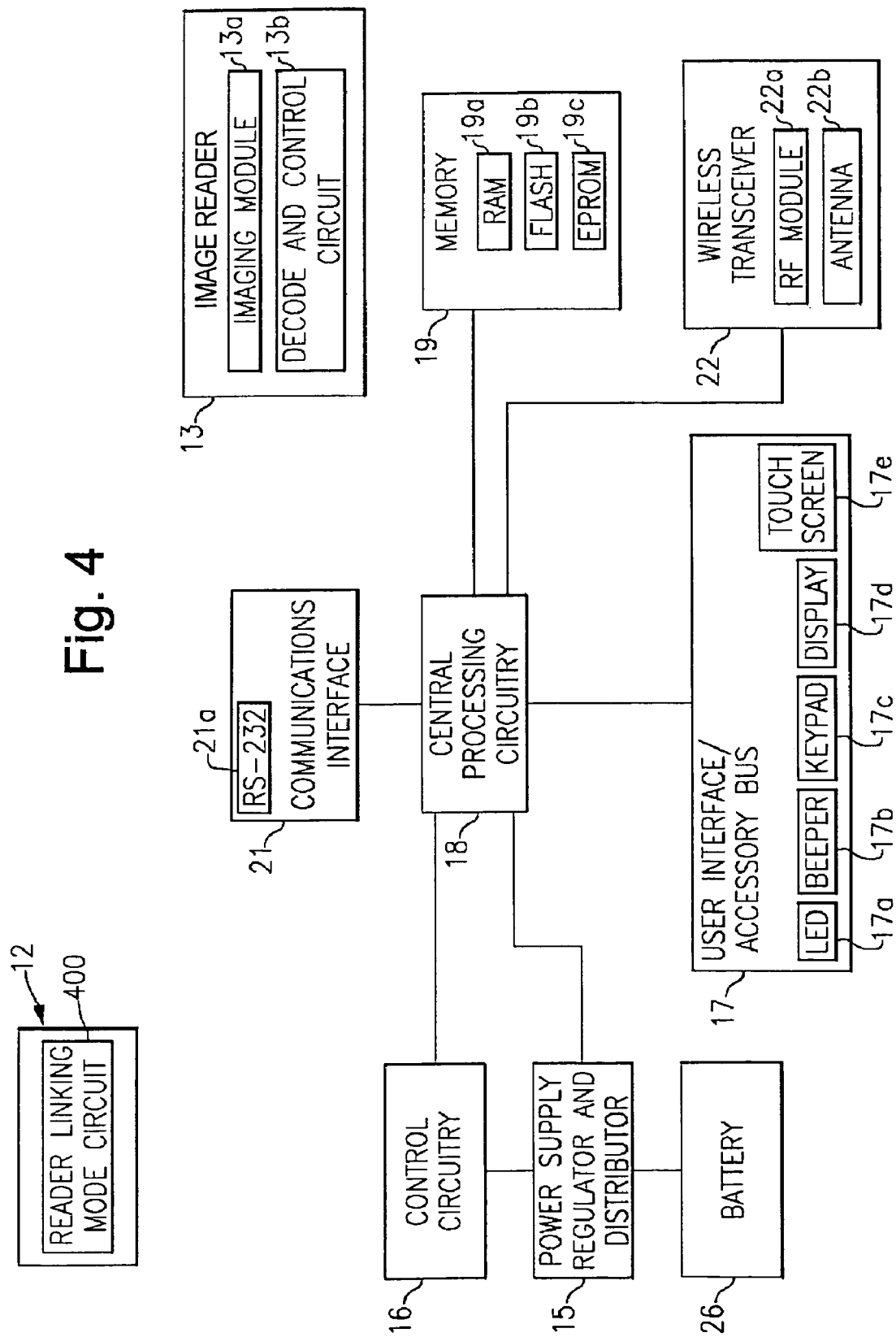
FIG. 4 is a schematic block diagram of an exemplary reader.

Referring to FIGS. 3 and 4, a plurality of reader systems may be used as part of a scanning system or indicia reader network 100. In an exemplary indicia reader network 100 a reader 12 scans an item's 102 information bearing indicia. The reader output signal of information contained in the indicia may be wirelessly communicated to the base unit 14 linked with the reader 12. The base unit 14 then communicates that indicia data message to a host device, such as a local server 110 through a local bus 116 which may decode the data message for further processing. The base unit 14 may communicate this bar code data to the local server 110 via a hardwired connection 106 such as, for example, a USB connection or a RS-232 serial connection. The local server 110 may communicate that information via a hub 112 to a remote server 114 that may perform a variety of functions and responsibilities.

The reader 12 may include a wireless transceiver 22, such as, for example a wireless Bluetooth, IEEE 802.11, ZigBee, or other standardized or proprietary RF device which may be configured to provide secure transaction communications between the reader 12 and the base unit 14. The wireless transceiver 22 may consist of an RF module and antenna (not shown) and is configured to engage in two-way communication with at least one other wireless transceiver. The other wireless transceiver 32 may be located in the base unit 14, which may be a stand-alone unit or physically incorporated into another host device such as a computer, a point of sale (POS) terminal, a transaction terminal, cash register, or similar device.

In an exemplary embodiment, the reader 12 may communicate with a PDA 170 or PDT which may act as a host device or it may communicate with a local server.

An exemplary reader system may combine the functions of multiple healthcare devices on a compact, mobile platform, such as a compact reader, PDA, PDT, cellular phone, or other platform.

For example, a nurse might wear a reader 12 around her neck using a lanyard, or she may slip it into her pocket. The reader 12 will provide access to healthcare information that is relevant for that worker. The information may exist on a Healthcare Information System (HIS) or other LAN or in the memory 19 in the reader 12.

The reader 12 may contain a bar code reader, such as an area imager, for the purpose of reading bar codes that identify the patient and the medication that is about to be administered to the patient. The patient ID bar code may be on a wristband like the one described in a previous patent application from Hand Held Products. The medication may be a unit dose package or it might be an IV bag. At a minimum the reader will have the ability to read the bar codes and provide feedback to the healthcare worker. The feedback may be in the form of an audible feedback and a color LED indicator.

One way to reduce the size and the power consumption of the reader may be to omit a keypad and display. Or the size of the keypad and display may be reduced to a minimal size that allows for simple interaction and message display as the worker is mobile. For example a small display might be adequate for communicating a short alarm or an alert to the nurse, but it may be too small to be adequate for viewing an electronic medical record (EMR). It may have a microphone and a speaker for relaying voice. The reader may be connected to a wireless LAN for the purpose of relaying voice or other messages. It may be used to allow a nurse to communicate directly with a doctor.

A worker at a point of care (POC) may need to view information such as an EMR on a larger display, use a keyboard, or other human input function in order to enter data into the HIS. At the POC the reader may wirelessly associate with a keyboard and display.

The reader 12 may be configured to contain elements or systems for enabling a mobile worker, such as a nurse to perform many functions. When it is docked, or associated with a POS station, it may complete a full workstation system, with all of the ensuing data interaction capabilities.

The mobile worker may carry a smaller reader with a battery life sufficient to cover a full shift. The reader may allow the mobile worker access to critical data and information while moving about. The reader may allow the worker access to a vast array of information and peripherals at the POC where those faculties are needed. The overall cost of the system may be minimized because it prevents duplication of hardware. At the POC, there is no need to duplicate the hardware that is in the reader, only to augment the reader with additional data I/O peripherals. At the POC, unauthorized people may not access the HIS because they don't have a reader that completes the system, thus they don't have access.

If the mobile reader runs out of battery life it may be dropped into a charging bay and replaced with another reader that is fully charged. Alternately the battery may be replaceable much like a power tool.

In an exemplary embodiment of the invention, the reader itself may be used to authenticate the user, since each user will be assigned to carry his own personal reader during his work shift. In another embodiment access to HIS data may be protected by an additional layer of security, such as input of a password or biometric identification, such as voice recognition, face recognition, iris identification, fingerprint identification, or other. The mobile reader may be constructed to capture the security input, or the POC station. The security may occur during the process of associating the mobile reader to the POS station.

In an exemplary embodiment of the invention, the POC station may provide access to different data depending on the credentials of the user who is connecting. For example, a nurse may have access to EMR data, while an engineer might only get access to a service program.

In an exemplary embodiment the patient can get access to patient specific data, such as food menu, billing information, status of an order for medication, or other. The display may be used as a TV or to deliver movies or games to the patient. Patient's family members may be able to access Do Not resuscitate (DNR) or other data.

In an exemplary embodiment the display has a means of limiting viewing angles for privacy.

In an exemplary embodiment the mobile readers form a mesh network, communicating peer-to-peer, thus reducing the need for access point infrastructure.

Some examples of data that could be viewed and modified at the POC station include allergies, vital signs, DNR, patient ID number or billing number, doctor name, current medication, a billing history, a drug or procedure history, or the patient chart/EMR.

Some examples of display types include an LCD monitor, projection display, TV, remote display of vital monitor at the POC, side-by-side panels projecting text and images, or a holographic projection.

Exemplary uses for a reader system may include nurse-doctor conversations, display of procedures for helping educate healthcare workers, as in a teaching hospital, or as part of a system that verifies the "Patient Rights" (right patient, right time/frequency of administration, right dose or blood type match, right route of administration, right medication).

Figure 8:
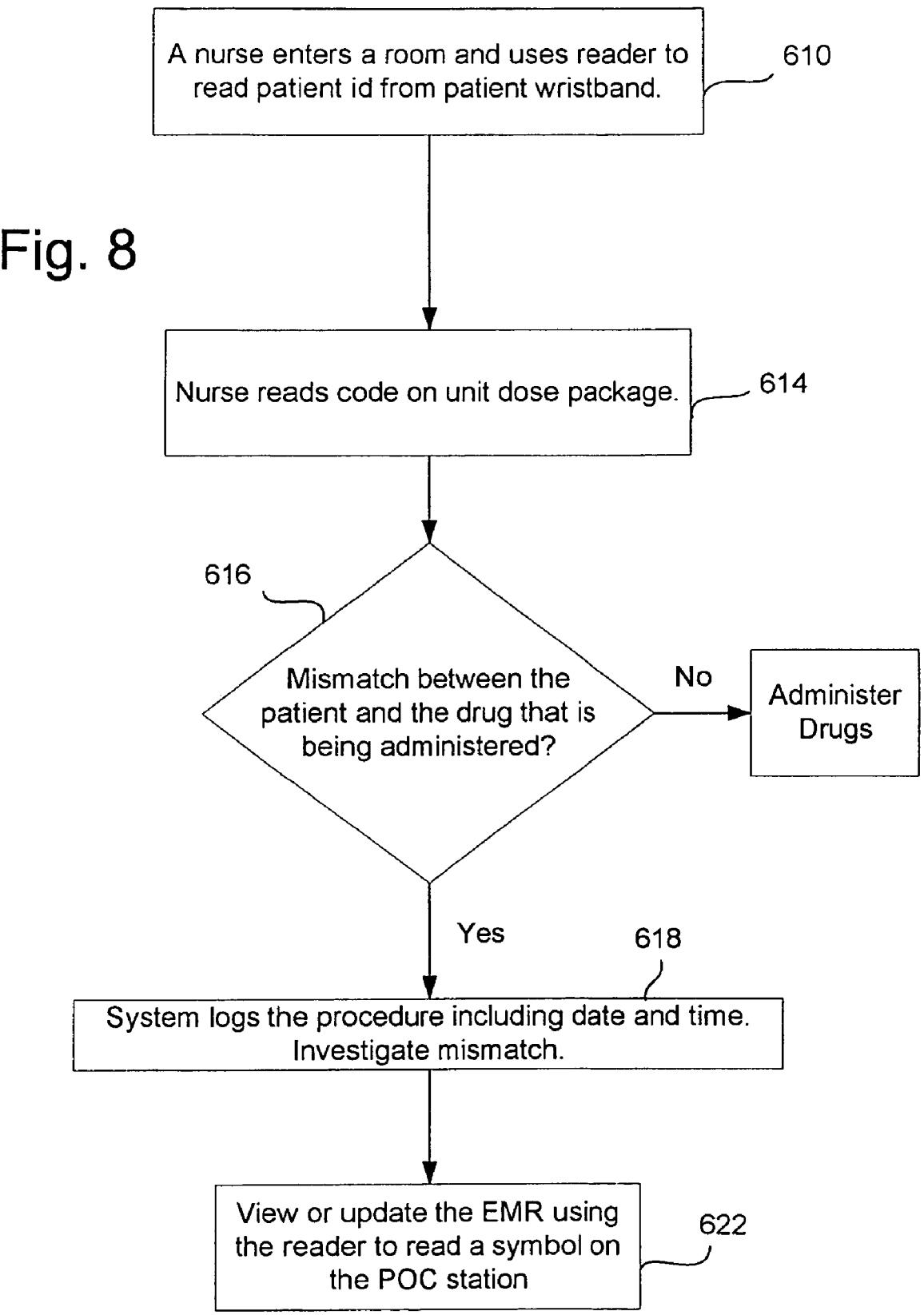
FIG. 8 is a flow diagram of an exemplary method of using a reader system.

FIG. 8 illustrates an exemplary method of using a reader system comprising the following steps:
1. A nurse enters a room and uses reader 12 to read patient ID from patient wristband. (610)
2. Nurse reads code on unit dose package. (614)
3. System compares the data from the reader 12 to the patient identification data and alerts nurse if there is a mismatch (616) between the patient and the drug that is being administered; if there is a mismatch, the system logs the procedure including date and time. (618)
4. If the nurse needs to view or update the EMR she simply uses the reader to read a bar code on the POC station and the two are automatically linked, permitting full interact with the HIS system, according to the nurses access rights. (622)
5. When the nurse leaves she may manually log out of the station, or the POC station may recognize that the mobile reader has moved away and may automatically disengage.

In an exemplary embodiment, the reader 12 may broadcast sensitive information such as personal records, medical information in healthcare, social security numbers, biometrics, entrance and access keys, ticketing applications, vouchers for discount in retail component specifications, recipes or process data in a production environment, or other financial or private information. In these type of applications the data is generally at risk from being misused and/or to perform criminal activity. A reader system with security features may reduce such risks. For these applications it may be required that the data being broadcast be encrypted, wherein the information bearing indicia can be read, but the data in the information bearing indicia is encrypted. Encryption is the conversion of data into a form that cannot be easily understood by unauthorized people. A decrypting algorithm would be required to decrypt such data. Decryption is the process of converting encrypted data back into its original form, so it can be understood. Operation of the decrypting algorithm requires the use of a "key". Encryption key(s) may be secret keys, private keys, or public keys. This encryption key may be provided in the reader 12 firmware, the host processor 118, in the encrypted barcode or in a separate barcode, which allows the user to decide whether to separate the encryption key from the data or combine them. Encryption keys may be associated by mathematical derivation, symmetry, or other relationship. Encryption keys may updated by pushing the key 11 on the reader 12, or by reader 12 to base unit 14 communication as discussed hereinbefore.

With reference now to FIG. 4 the image reader subassembly 13 may include an imaging module 13a and a decode and control circuit 13b. The central processing circuitry 18 may include image processing circuitry for evaluating a captured image to determine if it contains decodable indicia and for decoding indicia in the captured image. If the image processing circuitry 18 is able to decode indicia in the captured image, the image processing circuitry sends an electrical signal containing the decoded information to the wireless transceiver 22. In the embodiment shown, the wireless transceiver 22 includes a RF module 22a and an antenna 22b. The wireless transceiver 22 then transmits the decoded information to the wireless transceiver 32 in the base unit 14.

The reader 12 may be powered by a power source 26, such as, for example an AC source from a wall receptacle (e.g., 120VAC) or may be powered by a host device. In the present embodiment, the external power source 26 is connected to a power supply regulator and distributor 15, which is then connected to the control circuitry 16 and the central processing circuitry 18. Power may then be supplied to the other elements via the control circuitry 16 and the central processing circuitry 18. Alternatively, the power supply regulator and distributor 15 may be directly connected to the additional elements.

The reader 12 may include electronic memory 19 both for storing operating instructions and for storing captured images and for use in the processing of the captured images. The memory may, for example, include random access memory 19a, flash memory 19b, and erasable programmable read-only memory (EPROM) 19c which are illustrative of types of memory that may be used in the present invention and are in no way limiting to the scope of the invention and that other suitable memory types may be used.

The reader 12 may further include a user interface/accessory bus. The user interface 17 may include light emitting diodes (LEDs) 17a, a beeper 17b, a keypad 17c, a display 17d, a touch screen 17e, or combination thereof. In addition, the reader may also include a communications interface 21 (e.g., RS-232 port 21a), allowing for diagnostics of the reader.

Figure 5:
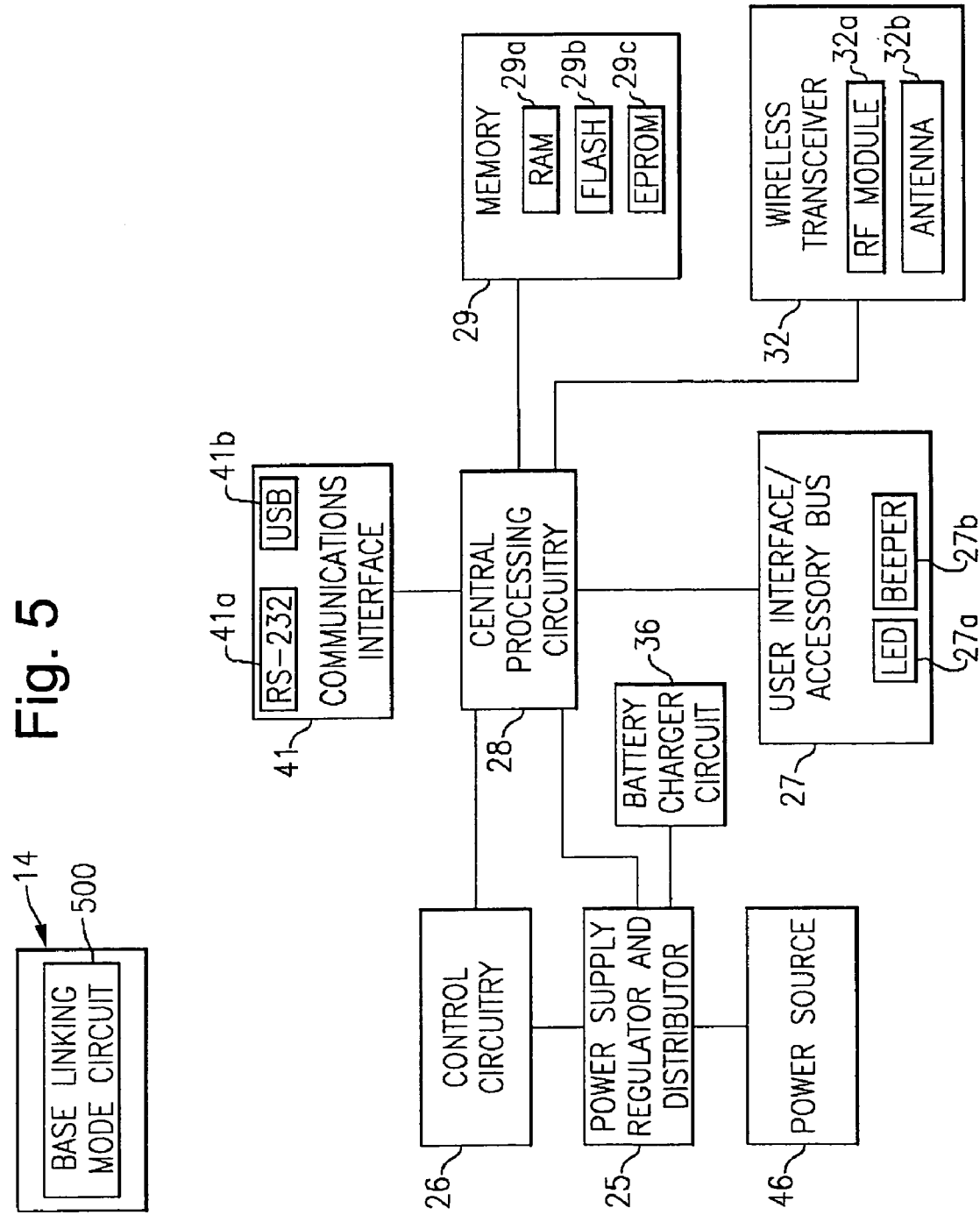
FIG. 5 is a schematic block diagram of an exemplary base unit.

Referring to FIG. 5, there is shown a schematic of exemplary electronic components of a wireless transceiver equipped base unit 14 in block diagram form. It will be appreciated by those of ordinary skill in the art that although the base unit 14 is described as separate functional components, the functions of any of the separate components may be combined. The base unit 14 includes central processing circuitry 28 and control circuitry 26 that may be incorporated into one or more printed circuit boards. The base unit 14 further may include a wireless transceiver 32, such as, for example a wireless Bluetooth, IEEE 802.11b, ZigBee, or other standardized or proprietary RF device. The wireless transceiver 32 consists of an RF module 32a and antenna 32b and may be configured to engage in secure two-way communication with at least one other wireless transceiver. The other wireless transceiver 22 may be located in at least one reader 12.

The base unit may be powered by a power source 46, such as, for example an AC source from a wall receptacle (e.g., 120VAC) or may be powered by a host device. In the present embodiment, the external power source 46 is connected to a power supply regulator and distributor 25, which is then connected to the control circuitry 26 and the central processing circuitry 28. Power may then be supplied to the other elements via the control circuitry 26 and the central processing circuitry 28. Alternatively, the power supply regulator and distributor 25 may be directly connected to the additional elements such as a battery charger circuit 36.

The base unit 14 may further include electronic memory 29 for storing operating instructions. The memory may, for example, include random access memory 29a, flash memory 29b, and erasable programmable read-only memory (EPROM) 29c. Many types of memory may be used depending upon the applicable design criteria without the need for undue experimentation.

The base unit may further include a user interface/accessory bus 27. The user interface may include light emitting diodes (LEDs) 27a and a beeper 27b, or any combination thereof. In addition, the base unit 14 may include a communications interface 41 (e.g., RS-232 port 41a and USB 41b), allowing for communications between the base unit 14 and a host device. Base unit 14 may be coupled to the local server 110 by electrical cabling connected through a local hub 116 to a communications port of the server 104.

The wireless reader system 10 may be configured for operation in a hostile environment. For example, if the wireless reader system 100 is to be used in a high humidity environment, both the reader 12 and the base unit 14 may be hermetically sealed units. The reader 12 may communicate with the base unit 14 using a communication system, such as, for example a free space infrared system when the reader 12 is docked to the base unit 14 in addition to communication via radio wireless transceivers. Alternatively, the reader 12 and the base unit 14 may be configured to communicate with one another using magnetic induction when the reader 12 is docked to the base unit 14.

It is noted that a typical indicia reader network 100 will include a plurality of points of transaction, and therefore a plurality of wireless readers 12 and base units 14. As discussed above, it is necessary to link the reader 12 with an individual base unit 14 to allow the reader 12 to communicate scanned indicia information to its base unit 14, which then communicates scanned information to the local server 110. This link may be made by programming the reader 12 with information identifying the particular base unit 14 so that the reader 12 directs its transmitted information to that base unit 14. Given the wireless nature of the communication between the readers 12 and base units 14, a linking method between the base unit 14 and the reader 12 may ensure that the communication of an item's 102 bar code data message at a particular point of transaction be communicated to the base unit 14 associated with the host device 104 at that point of transaction and no others.

Figure 6A:
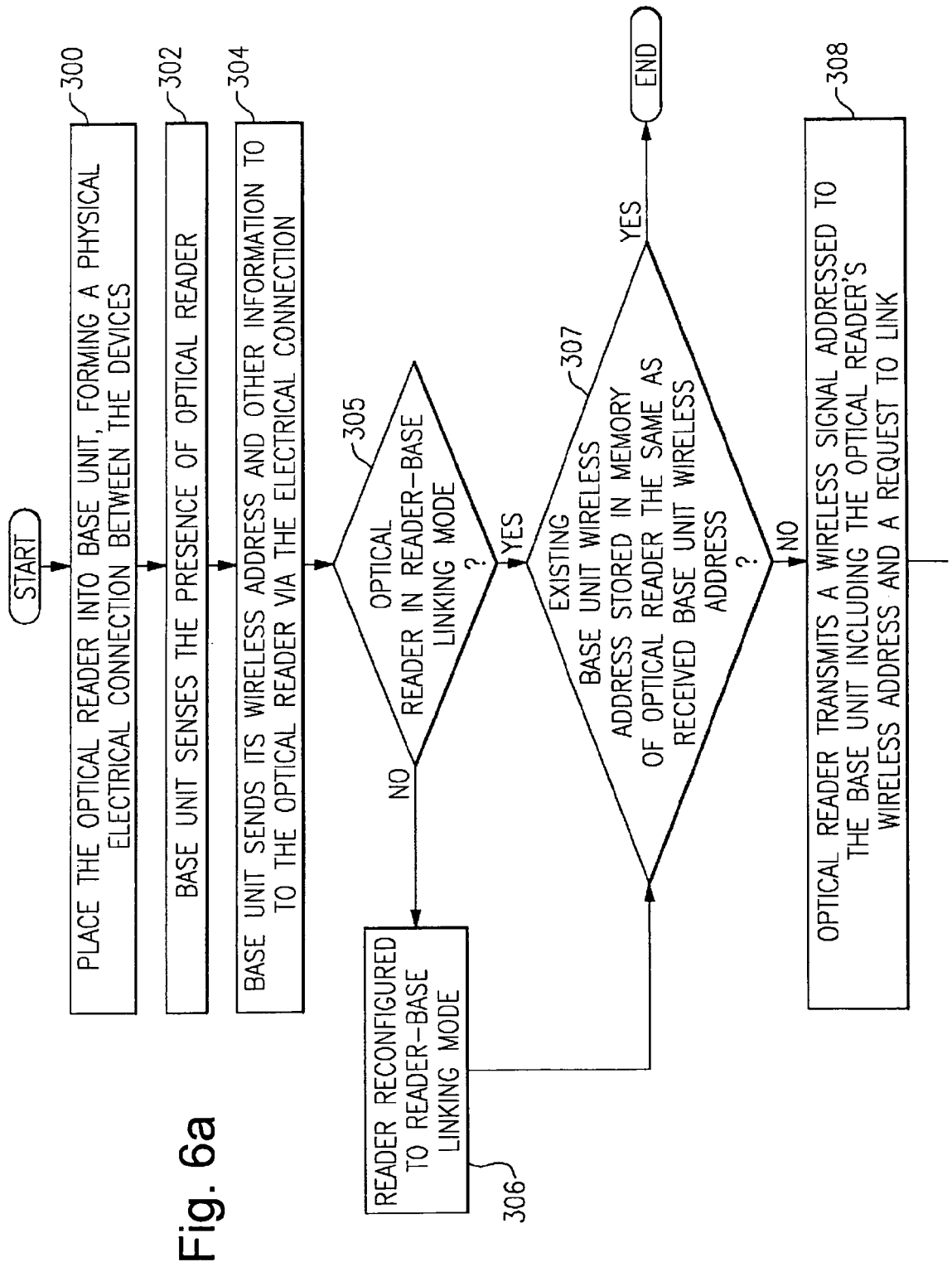
FIGS. 6a and 6b are flow diagrams of an exemplary method of linking an exemplary reader and an exemplary base unit.
Figure 6B:
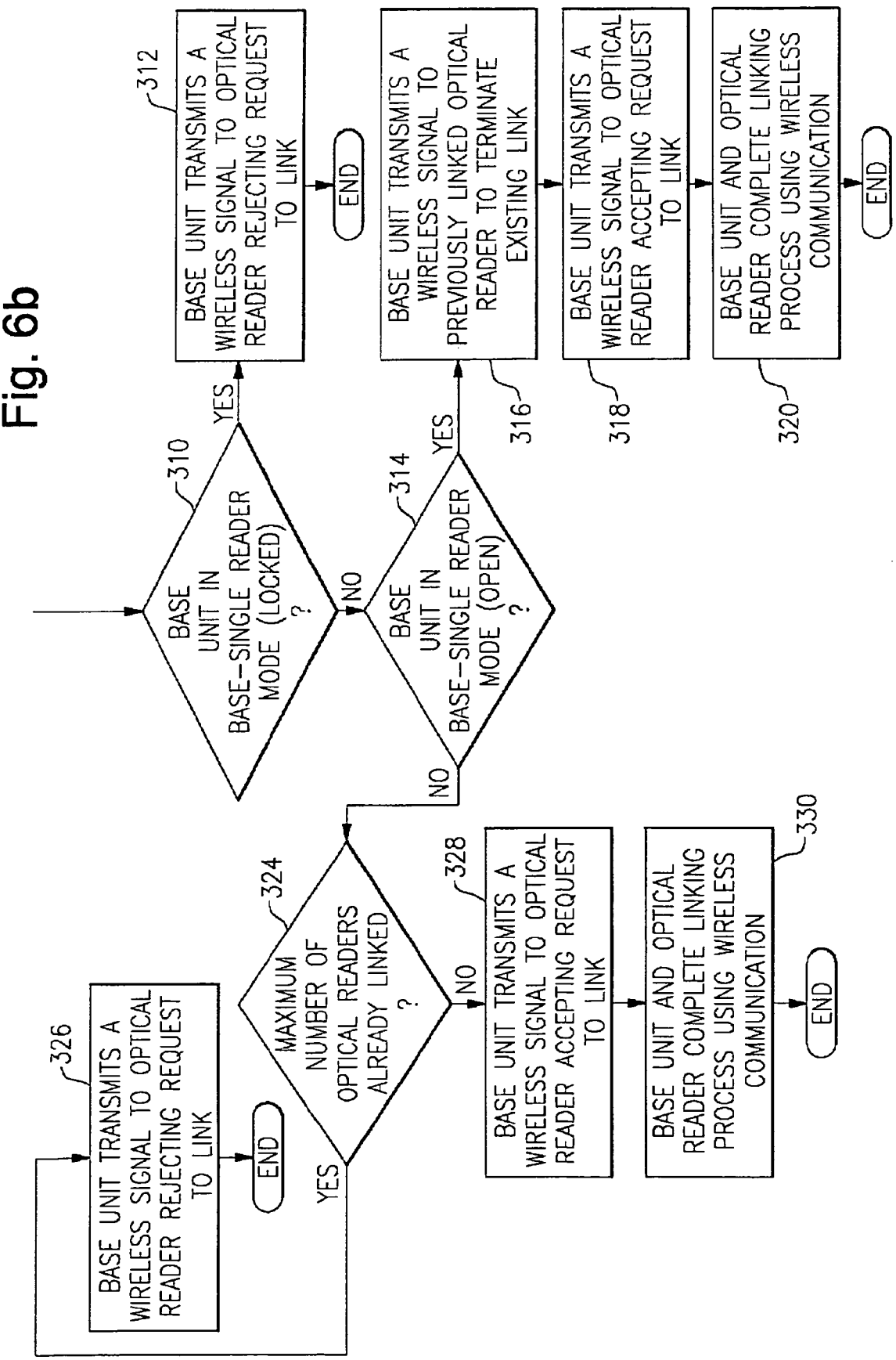

FIGS. 6a and 6b are exemplary flow diagrams illustrating the operation of the method of linking the wireless reader 12 with a base unit 14. The user initiates the linking process at a step 300 (time t0) by placing the reader 12 into the base unit 14, establishing a temporary physical electrical connection between the two devices. When the reader is engaged with the base unit, the base unit 14 may transmit information to the reader 12 without using a wireless system. Prior to time t0 the reader 12 is not in the base unit 14.

At step 302 (time t1), the base units 14 central processing circuitry 28 senses the presence of the reader 12 in the base unit 14.

At a step 304 (time t3), the base units 14 central processing circuitry 28 sends the address of the base units 14 wireless transceiver 32, along with other control information. Bluetooth wireless communication protocol may be used, with each reader 12 and each base unit 14 assigned a unique identifier or address. Although an embodiment using Bluetooth technology is described, it should be noted that IEEE 802.11, ZigBee, or other standardized or proprietary RF technology may also be used in the present invention. In order for the reader 12 to begin communicating wirelessly with the base unit 14, it must receive the base units 14 unique Bluetooth address. With the reader 12 placed in the base unit 14, the base unit 14 may transmit its address to the reader 12 using a serial communication. Once the reader 12 has received the base units 14 address, the reader 12 need no longer be physically coupled with the base unit 14 since the remainder of linking communications take place wirelessly.

At a step 305, the reader 12 determines whether it is presently configured to link with a base unit 14. The reader 12 may be configured to operate in a plurality of user-selectable modes for linking a wireless reader with either a base unit 12 or other wireless device. If the reader 12 is configured in its "reader-base linking mode," the user is required to temporarily physically couple the reader and base unit together in order to initiate the linking process, and the reader 12 may only be linked with devices that may be physically coupled with the reader 12 to form a physical electrical connection. For other applications where the wireless reader 12 is to be linked with a device that cannot necessarily be physically coupled with the reader 12, the reader 12 may be configured in a "reader-free linking mode" where the linking of the two wireless devices is accomplished without a physical connection. The reader 12 may be regarded as having various processing circuits (modules), including reader linking mode circuit 400, that may be provided by appropriately programming central processing circuitry 18 with a program stored in memory 19 to monitor and control the reader 12. Based on the results of this monitoring and control, the reader linking mode circuit 400 may then configure the reader 12 to operate in "reader-base linking mode" or "reader-free linking mode."

Similarly, the base unit 14 may be regarded as having various processing circuits (modules), including base linking mode circuit 500, that may be provided by appropriately programming central processing circuitry 28 with a program stored in memory 29 to monitor and control the base unit 14. Based on the results of this monitoring and control, the base linking mode circuit 500 may then configure the base unit 14 to operate in "reader-base linking mode" or "reader-free linking mode"

At step 305, if the reader is configured in "reader-base linking mode," the linking process continues. If it is not, at a step 306, the reader 12 is reconfigured to operate in "reader-base linking mode" using the control information sent by the base unit 14.

At a step 307, the central processing circuitry 18 of the reader 12 then compares the received base unit 14 address with the base unit 14 address, if any, already stored in memory 19. If the addresses are the same, there is no need to link the reader 12 with the base unit 14 and the process is complete.

If there is no existing base unit 14 address or the stored address is different than the newly received address, at a step 308, the wireless transceiver 22 of the reader 12 assumes a Bluetooth Master role and goes into a Page Mode while the wireless transceiver 32 of the base unit 14 assumes a Bluetooth Slave role and goes into Page Scan Mode. The reader 12 transmits a wireless signal addressed to the base unit 14. The wireless signal includes information about the reader 12 that allows the base unit 14 to communicate with the reader 12.

For example, when a Bluetooth wireless system is used, the information contained in the wireless signal will include the unique address of the wireless transceiver 22 of the reader 12 as well as a request to link.

After the base unit 14 receives the wireless signal from the reader including the reader's 12 wireless address and a request the link, the base unit 12 determines whether to reject or accept the request to link in decision block 310. This determination is based upon which linking mode the base unit 12 is configured to operate in. The base unit 14 may be capable of operating in at least three different linking modes, either where only one reader 12 may be linked with a base unit 14 ("base-single reader mode (locked)" or "base-single reader mode (open)") or where more than one reader 12 may be linked with a base unit 14 ("base-multiple reader mode") at any one time. The base unit 14 may be programmed to function in any of these modes by using an already linked reader 12 to scan an appropriate bar code label 311, 313, 315, or 317 associated with each mode to configure the base unit 14 to operate in that mode. The base unit 14 may be regarded as having various processing circuits (modules), including a base linking mode circuit that may be provided by appropriately programming central processing circuitry 28 with a program stored in memory 29 to monitor and control the base unit and its wireless transceiver 32. Based on the results of this monitoring and control, the reader linking mode circuit may then configure the base unit 14 to operate in "base-single reader mode (locked)," "base-single reader mode (open)," or "base-multiple reader mode"

For example, to operate the base unit 14 to communicate only with a single reader 12, a user will encounter one of two conditions: "base-single reader mode (locked)" and "base-single reader mode (open)"). In "base-single reader mode (locked)," once a reader 12 is linked with a base unit 14, other readers 12 are blocked from linking to the base unit 14 if they are inadvertently placed into the base unit 14. To operate in "base-single reader mode (locked)," an already linked reader 12 scans a "base-single reader mode (locked)" bar code label 311. The information contained in the bar code label 311 causes the reader to be or remain configured in the default "reader-base linking mode," whereby the reader 12 may only be linked with devices that may be physically coupled with the reader 12. The information contained in the bar code label 311 is also transmitted to the base unit 14, configuring the base units linking mode switching circuit so that other readers 12 may not link with the base unit 12.

At a step 310, the base unit 14 determines whether it is operating in "base-single reader mode (locked)" If it is, at a step 312, the base unit 14 rejects the readers 12 request to link and transmits the rejection to the reader 12, terminating the linking process. When the reader 12 receives this rejection, it removes the wireless address associated with that base unit 14 from its memory.

If the base unit 14 is not in "base-single reader mode (locked)," at step 314, it next determines if it is in "base-single reader mode (open)" In "base-single reader mode (open)," when a reader 12 is placed in the base unit 14, the existing link established in the base unit 14 is removed and a new link is established. To operate in "base-single reader mode (open)," the already linked reader 12 scans the "base-single reader mode (open)" bar code label 313. The information contained in the bar code label 313 causes the readers linking mode switching circuit to be or remain configured in the default "reader-base linking mode," whereby the reader 12 may only be linked with devices that may be physically coupled with the reader 12 to form a physical electrical connection. The information contained in the bar code label 313 is also transmitted to the base unit 14, configuring the base units 14 linking mode switching circuit so that the existing link is removed when establishing the new link.

If at step 314, the base unit 14 is in "base-single reader mode (open)," at a step 316, the base unit 14 transmits a wireless signal to the previously linked reader 12 to terminate the existing link. At a step 318, the base unit 14 then transmits a wireless signal to the new reader 12, including an acceptance of the request to link as well as any additional information to complete the linking process. At a step 320, the reader 12 and base unit 14 complete the linking process using wireless communication.

If the base unit 14 is not in "base-single reader mode (open)" and, as already has been determined at step 308, is not in "base-single reader mode (locked)," by default, the base unit 14 is in "base-multiple reader mode" To cause the base unit 14 operate in "base-multiple reader mode," the linked reader 12 scans a "base-multiple reader mode" bar code label 315. The information contained in the bar code label 315 causes the reader 12's linking mode switching circuit to be or remain configured in the default "reader-base linking mode," whereby the reader 12 may only be linked with devices that may be physically coupled with the reader 12 to form a physical electrical connection. The information contained in the bar code label 315 is also transmitted to the base unit 14, configuring the base units 14 linking mode switching circuit to allow multiple readers 12 to be linked with the base unit 14. A predetermined limit may be placed on the number of readers 12 that may be linked with a base unit. This limit may be a function of the number of reader 12 wireless transceivers 22 that the base unit 14 wireless transceiver 32 may communicate with (for example, seven). Once that limit is reached, the base unit 14 will not allow linking of another reader 12 until one of the readers 12 is unlinked. A reader 12 may be unlinked from the base unit 14 by scanning an "unlink" bar code label 317, causing the base unit 14 to both communicate the unlinking to the reader 12, which will then delete the address of the base unit 14, and then delete the information associated with that particular reader 12. It should be pointed out that in "base-multiple reader mode," while the base unit 14 may accommodate multiple readers 12, each reader 12 only communicates with a single base unit 14.

If the base unit 14 is in "base-multiple reader mode," at step a 324, the base unit 14 determines whether the maximum number of readers 12 is already linked to the base unit 14. If the maximum number of linked readers 12 has already been reached, at a step 326, the base unit 14 rejects the readers 12 request to link and transmits the rejection to the reader 12, terminating the linking process. When the reader 12 receives this rejection, it removes the wireless address associated with that base unit 14 from its memory. If the maximum number of readers 12 has not been reached, at a step 328, the base unit 14 then transmits a wireless signal to the new reader 12, including an acceptance of the request to link as well as any additional information to complete the linking process. At a step 330, the reader 12 and base unit 14 complete the linking process using wireless communication.

After the initial linking is complete, the wireless transceiver 22 of the reader, still in the Bluetooth Master role, may initiate another linking process to switch roles with the wireless transceiver 32 of the base unit, which may then assume the Bluetooth Master role. The reader 12 and/or base unit 14 may be programmed to emit an audio signal or beep when the linking process is complete by momentarily activating a speaker.

In the linking method described above, the reader is configured in a default "reader-base linking mode," whereby its mode switching circuit configures the reader 12 to only link with base units 14 or other devices that may be physically coupled with the readers connector to form a physical electrical connection between the devices to enable the linking process to take place. In addition to linking with a base unit 14 at a point of transaction in its default "reader-base linking mode," the reader 12 of the preferred embodiment may also communicate directly with other devices that include a wireless transceiver capable of Bluetooth communication or are coupled with a USB dongle utilizing the Bluetooth communications standard. As mentioned above, examples of these other devices include a personal digital assistant (PDA), a portable data terminal (PDT), or similar device. For example a reader 12 could be used as an input device by an indicia reader manager with a PDT 170 containing information about patients. As the reader 12 scans the bar codes associated with each patient or medication, the PDT 170 receives this bar code and displays the information associated with the patient or medication. In order to enable this communication, however, the reader 12 and PDT 170, or other device, must be linked. In the likely event that PDT 170 or other device does not have a connector to mate with the connector of the reader 12 to initiate the linking process described above (i.e., transferring the address to the reader 14 through the connection), a secondary linking process is required.

To enable this secondary linking process, the reader 12 must be placed in "reader-free linking mode" In "reader-free linking mode," the reader 12 provides indication to other host devices that it is available for linking. In order to cause the readers 12 reader mode linking circuit to configure the reader 12 to operate in "reader-free linking mode," similar to other configuration procedures discussed above, the reader 12 may scan a "reader-free linking mode" bar code label. The information contained in the bar code label causes the reader mode linking circuit to configure the reader 12 to begin operating as a Bluetooth Slave in Broadcast mode. Alternatively, the reader 12 may be placed into "reader-free linking mode" in a variety of other ways.

The readers 12 user interface/accessory bus 17 may include a number of user interfaces that would allow a user to configure the reader to operate in "reader-free linking mode" using a keypad 17c, a display 17d, a touch screen 17e, or any combination thereof. For example, the reader 12 could provide a graphical user interface (GUI) to allow the user to switch between different reader linking modes by selecting appropriate icons.

Once the reader 12 has been configured to operate in "reader-free linking mode," it begins to transmit messages, including the name of the reader 12 as well as the address of its wireless transceiver 22, to inform any nearby Bluetooth devices that it is available for linking. The other device, such as a PDT 170, in the broadcast area and set in Discovery Mode will be informed of the reader 12.

Acting as a Bluetooth Master, the PDT 170 may initiate the linking process of the wireless transceivers by communicating its address to the reader 12 and following the process described above. After the reader 12 and the PDT 170 have been linked, information scanned by the reader 12 will be transmitted to the other device. When the user no longer wishes to operate the reader 12 in "reader-free linking mode," that user may reconfigure the reader 12 to operate in "reader-base linking mode" using any of the methods described above, including scanning appropriate bar code labels or using a graphical user interface. In addition, the user may simply place the reader into a base unit 14 to initiate the linking process as described above and shown in the flow diagrams. At step 305 of the process, if the reader 12 is in "reader-free linking mode," at step 306, the reader 12 will be reconfigured into "reader-base linking mode"

It is to be noted that the Bluetooth wireless communication protocol referenced hereinbefore may be encrypted further according to the FIPS standard, such as the FIPS 140-2 standard.

Figure 7:
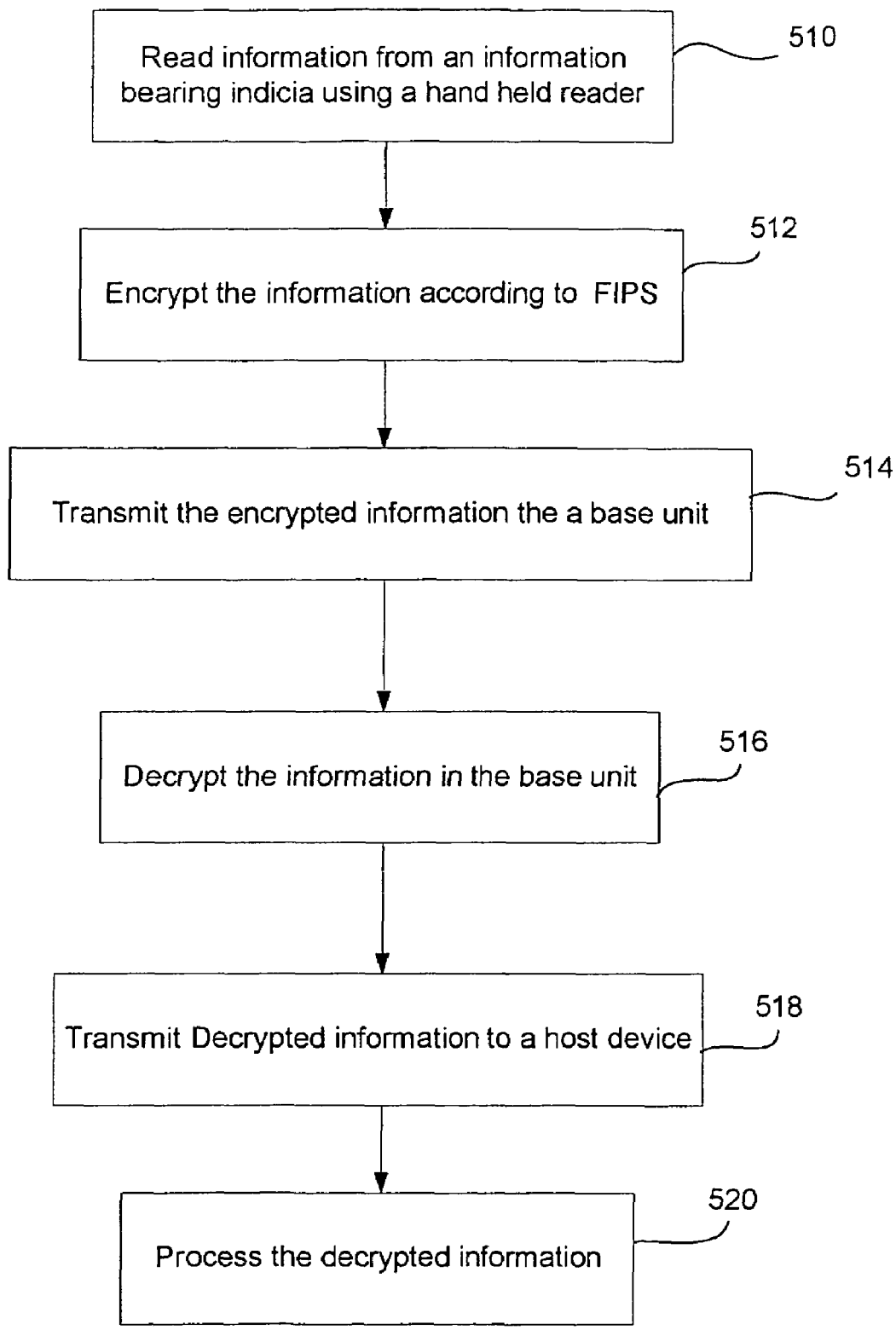
FIG. 7 is a flow diagram of an exemplary method of linking an exemplary reader and an exemplary base unit.

Utilizing this exemplary standard, a cordless scanner and base station system may communicate wirelessly, and may protect transmitted sensitive data using the flowchart illustrated in FIG. 7:

i) A hand held scanner reads information from an information bearing indicia (510).

ii) The scanner encrypts the information according to a FIPS standard (512).

iii) The encrypted information is transmitted to a base unit (514). The scanner and base station may use a public/private key pair to use for encrypting and decrypting data or a key agreement algorithm). To this end, random number generators and encryption algorithms may be used to generate, share, and establish keys. Once the two components have established a shared private key, the scanner will encrypt a known text message and transmit it to the base to verify that the keys match. Once the private key is shared successfully, and encryption is enabled, wireless data passing between the base and the scanner will be encrypted.

iii) The base unit decrypts the information (516) using the established key.

iv) The decrypted information is transmitted to a host device (518).

v) The decrypted information is processed by the host device (520).

The scanner and base station may perform self tests. Two exemplary self tests that may be performed are:
a. power-on self tests performed at power up, wherein the encryption algorithms are tested using known answer tests (KAT) that will use known message and keys and firmware is tested to ensure that it has not been modified. This integrity test may be performed using a digital signature or message authentication code algorithm.
b. conditional self tests performed when an appropriate condition is satisfied, wherein the random number generator will be tested each time it is used to ensure that every number generated is different that the previous generated value and upon loading external firmware the scanner or base station verifies the authenticity of the incoming firmware using a digital signature. When a key algorithm agreement is implemented, a verification ensures that shared public keys are matched to their private key counterparts. The state of the encryption module (enabled or disabled) may be tested every time the module is enabled or disabled.

A cryptographic module performing the tasks described above is not limited to a single implementation. The cryptographic module may be (but is not limited to) one of the following exemplary implementations:
i) A software only cryptographic module which does not require any hardware changes.
ii) A custom communications module (radio) which incorporates FIPS 140-2 compliant security functions that will replace an existing communications module.
iii) A standalone cryptographic module consisting of additional hardware and software that interacts with the existing hardware, software, and communications modules.

The FIPS 140-2 Level 1 security requirements policy describes security parameters as required in the Federal Information Processing Standards Publication 140-2 published by the National Institute of Standards and Technology (NIST) and the United States Department of Commerce.

More information about NIST and the cryptographic module validation program can be found at http://csrc.nist.gov/cryptval/.

An imager and base station may communicate over a wireless Bluetooth connection wherein the hand held imager may be used for scanning and decoding barcodes or taking images. When enabled, the cryptographic module will encrypt and decrypt data that is transmitted between the base station and the cordless imager.

An exemplary cryptographic module providing FIPS 140-2 may provide encryption algorithms including AES, 3DES or HMAC-SHAL. The module may also perform ANSI X9.31 approved pseudo-random number generation. A HMAC-SHA1 signature may be used to verify that firmware has not been modified.

The cryptographic module may be built into the firmware of the reader as a multi-chip standalone cryptographic module wherein the firmware may be stored in flash memory, executed in a general purpose processor, and temporary data stored in RAM.

The reader may be configured to enable encryption through the use of menu settings. These settings may be configured using configuration barcodes, serial commands, or through custom default settings.

If the initialization is successful the base station and cordless scanner may make a successful beep, if initialization fails the base station and the cordless scanner will make an error beep.

A cryptographic module supports two roles: User and Crypto-Officer. The roles are implicitly assumed by any physical or automated entity that can interact with the base station and cordless scanner system.

| FIG. 2: Table of Roles and Associated Authorized Services | |
|---|---|
| Role | Authorized Services |
| User | All services except configuration and zeroization |
| Crypto-Officer | All services |

The module meets the FIPS 140-2 security level 1 requirements for the User and Crypto-Officer. Security level 1 requirements do not require any identification or authentication.

The following table describes services provided by a cryptographic module.

| FIG. 3: Authorized Services | | | |
|---|---|---|---|
| Service | Critical Security Parameter | Algorithm | Authorized Role |
| Symmetric Encryption / Decryption | Symmetric Key | AES | User, Crypto Officer |
| Message Digest | HMAC Key | HMAC-SHA1 | User, Crypto Officer |
| Random Number Generator | Seed Key | ANSI X9.31 | User, Crypto Officer |
| Key Establishment | Asymmetric Public and Private Keys | Diffie-Hellman | User, Crypto Officer |
| Show Status | none | none | User, Crypto Officer |
| Self Tests | none | none | User, Crypto Officer |
| Configuration | none | none | Crypto Officer |
| Zeroization of Keys | none | none | Crypto Officer |

FIPS 140-2 security level 1 may not require the cryptographic module to employ authentication mechanisms to control access to the module. The scanner implicitly sets the user role for a user in normal operation. The user can explicitly select the Cryptographic Officer role through a configuration or zeroization command. The command can be input through either scanning a configuration barcode or by serially sending a configuration command.

The cryptographic module may be designed and implemented specifically for use with a cordless, multi-threaded, and interrupt-driven operating environment.

The cryptographic module or other cryptographic security parameters may not be accessible to certain processes and components of the device firmware (such as drivers) while the module is operational.

The cryptographic module may incorporate an FIPS 140-2 approved firmware integrity test. The test calculates a digital signature of the firmware stored in ROM and compares that result to a known-good value. In the event that the digital signatures do not match the test fails and the cryptographic module will enter the error state.

The random number generator used in the cryptographic module may meet ANSI X9.31 standards. Each time the random number generator is active it may perform a self test which compares the current generated value to the previous generated value. If any two consecutive random values are equal then the test will fail and the module enter the error state.

The secret encryption and decryption keys used in AES may be generated and established using a Diffie-Hellman key exchange method in the cryptographic module. This method allows two modules with no prior knowledge of each other to establish a shared secret key over an insecure communications channel. Using the Diffie-Hellman method each module starts with a known secret value a and b respectively. They share a known prime number p and base number g. The modules each calculate ($g^a$ mod p) or ($g^b$ mod p) and the resulting values are shared. The modules then calculate the shared secret key since ($g^a$ mod p)$^b$=($g^b$ mod p)$^a$.

Internal or external keys may not be entered or output from the cryptographic module. Keys may be generated using FIPS approved methods.

The only key that that may be stored in ROM is the HMAC-SHA1 key.

Keys that are generated can be zeroized by a cryptographic officer operator using a special command which can be input through a serial interface or through scanning a barcode with the command embedded into it.

The power-on self-tests may verify that the firmware stored in flash ROM has not been modified or that the digital signature of the flash file is calculated and matches the known value.

Once the digital signature of the firmware is verified, known-answer tests are performed on cryptographic algorithms.

Pair-wise consistency tests may be performed when cryptographic keys are generated. Using the encryption key, the cryptographic module may encrypt a plaintext value. The resulting ciphertext may then be compared to the original plaintext. If the two values match then the test will fail and the key cannot be used.

Continuous random number generator test may be performed each time a random number is generated. The first number generated after power up may not be used, but may be stored. The second number generated may be compared to the first number, if the two numbers match the test will fail and the module may enter the error state. Each subsequent generated number may be compared with the previously generated number. The test will fail if any two compared values are equal.

Bypass Tests may be performed when a switch takes place between an exclusive bypass service and an exclusive cryptographic service. This transition occurs when the user changes a menu setting to disable encryption, a scanner is unlinked from a base, or once a scanner and base establish keys and begin encrypting data. The bypass test may consist of two tests: one for switching to enable encryption and one for bypassing encryption. The encryption enabled test may be a known answer test where a known ciphertext value may be tested against the output of the cryptographic module. The encryption disabled test may test plaintext against the output of the cryptographic module. If either test fails the module will enter the error state.

A cryptographic module may be a set of hardware, software, firmware, or some combination thereof that implements cryptographic functions or processes, including cryptographic algorithms and, optionally, key generation, and is contained within a defined cryptographic boundary. A cryptographic module may implement at least one Approved security function used in an Approved mode of operation. Non-Approved security functions may also be included for use in non-Approved modes of operation. The operator may be able to determine when an Approved mode of operation is selected. For Security Levels 1 and 2, the cryptographic module security policy may specify when a cryptographic module is performing in an Approved mode of operation. For Security Levels 3 and 4, a cryptographic module may indicate when an Approved mode of operation is selected.

A cryptographic boundary may consist of an explicitly defined perimeter that establishes the physical bounds of a cryptographic module. If a cryptographic module consists of software or firmware components, the cryptographic boundary may contain the processor(s) and other hardware components that store and protect the software and firmware components. Hardware, software, and firmware components of a cryptographic module can be excluded from the requirements of this standard if shown that these components do not affect the security of the module.

Authentication mechanisms may be required within a cryptographic module to authenticate an operator accessing the module and to verify that the operator is authorized to assume the requested role and perform services within that role. Depending on the security level, a cryptographic module may support at least one of the following mechanisms to control access to the module: Role-Based Authentication: If role-based authentication mechanisms are supported by a cryptographic module, the module may require that one or more roles either be implicitly or explicitly selected by the operator and may authenticate the assumption of the selected role (or set of roles). The cryptographic module is not required to authenticate the individual identity of the operator. The selection of roles and the authentication of the assumption of selected roles may be combined. If a cryptographic module permits an operator to change roles, then the module may authenticate the assumption of any role that was not previously authenticated.

Identity-Based Authentication: If identity-based authentication mechanisms are supported by a cryptographic module, the module may require that the operator be individually identified, may require that one or more roles either be implicitly or explicitly selected by the operator, and may authenticate the identity of the operator and the authorization of the operator to assume the selected role (or set of roles). The authentication of the identity of the operator, selection of roles, and the authorization of the assumption of the selected roles may be combined. If a cryptographic module permits an operator to change roles, then the module may verify the authorization of the identified operator to assume any role that was not previously authorized.

A cryptographic module may permit an authenticated operator to perform all of the services allowed within an authorized role, or may require separate authentication for each service or for different sets of services. When a cryptographic module is powered off and subsequently powered on, the results of previous authentications may not be retained and the module may require the operator to be re-authenticated.

Various types of authentication data may be required by a cryptographic module to implement the supported authentication mechanisms, including (but not limited to) the knowledge or possession of a password, RN, cryptographic key, or equivalent; possession of a physical key, token, or equivalent; or verification of personal characteristics (e.g., biometrics). Authentication data within a cryptographic module may be protected against unauthorized disclosure, modification, and substitution.

The initialization of authentication mechanisms may warrant special treatment. If a cryptographic module does not contain the authentication data required to authenticate the operator for the first time the module is accessed, then other authorized methods (e.g., procedural controls or use of factory-set or default authentication data) may be used to control access to the module and initialize the authentication mechanisms.

The strength of the authentication mechanism may conform to the following specifications:

For each attempt to use the authentication mechanism, the probability may be less than one in 1,000,000 that a random attempt will succeed or a false acceptance will occur (e.g., guessing a password or PIN, false acceptance error rate of a biometric device, or some combination of authentication methods).

For multiple attempts to use the authentication mechanism during a one-minute period, the probability may be less than one in 100,000 that a random attempt will succeed or a false acceptance will occur.

Feedback of authentication data to an operator may be obscured during authentication (e.g., no visible display of characters when entering a password).

Feedback provided to an operator during an attempted authentication may not weaken the strength of the authentication mechanism.

It will be apparent to those skilled in the art that various modifications and variations may be made to the present invention without departing from the spirit and scope of the invention. Thus it is intended that the present invention cover the modifications and variations of this invention provided they come within the scope of the appended claims and their equivalents.

The invention claimed is:

1. A health care service (HCS) network comprising:
a hand held optical reader for reading a target having information bearing indicia provided thereon and generating therefrom a decoded out indicia data message, the hand held optical reader having a first wireless transceiver and a display;
a base unit for receiving the decoded out indicia data message and transmitting the decoded out indicia data message, the base unit having a second wireless transceiver;
a workstation in communication with a server for receiving the decoded out indicia data message from the base unit and temporarily storing the decoded out indicia data messages;
wherein the HCS network is configured so that the hand held indicia reader reads the indicia symbol and transmits the decoded out indicia data message using the first wireless transceiver, the base unit receives the decoded out indicia data message using the second wireless transceiver and transmits the decoded out indicia data message to the server;
wherein the HCS network is configured so that the server communicates non indicia data messages with the base unit and the base unit communicates the non indicia data messages with the optical reader;
wherein the optical reader display is configured to display non indicia data messages originating from the server; and,
wherein the HCS network is configured so that the hand held indicia reader and the base unit have a linking mode wherein a request to link is sent from the optical reader to the server through the base unit by way of wireless communication to associate the optical reader with the server.

2. A health care service (HCS) network according to claim 1, wherein the non indicia data messages comprise at least one of the following: text messages; audio messages; audio alerts; vibratory alerts; and images.

3. A health care service (HCS) network according to claim 1, wherein the non indicia data messages have a unique identifier for receiving only by the optical reader.

4. A health care service (HCS) network according to claim 1, wherein the linking mode comprises linking when the optical reader is placed in the base unit.

5. A health care service (HCS) network according to claim 1, wherein the linking mode comprises linking by the optical reader decoding an indicia located on the base unit.

6. A health care service (HCS) network according claim 1, wherein the display capability is limited to 150 characters of 6 point font.

7. A health care service (HCS) network according claim 1, wherein the target is located at a patient point of care.

8. A health care service (HCS) network according claim 1, wherein the optical reader is capable of reading biometric data.

9. A health care service (HCS) network according claim 1, wherein at least one of the indicia data message and non indicia data message are encrypted.

10. A health care service (HCS) network according claim 1, wherein at least one of the indicia data message and non indicia data message are encrypted according to a FIPS140 standard.

11. A method of operating a health care service (HCS) network comprising:
reading a target having information bearing indicia provided thereon with a hand held optical reader and generating therefrom a decoded out indicia data message, the hand held optical reader having a first wireless transceiver and a display;
receiving the decoded out indicia data message and transmitting the decoded out indicia data message with a base, the base unit having a second wireless transceiver;
receiving the decoded out indicia data message from the base unit with a workstation in communication with a server;
temporarily storing the decoded out indicia data messages;
wherein the HCS network is configured so that the hand held indicia reader reads the indicia symbol and transmits the decoded out indicia data message using the first wireless transceiver, the base unit receives the decoded out indicia data message using the second wireless transceiver and transmits the decoded out indicia data message to the server;
wherein the HCS network is configured so that the server communicates non indicia data messages with the base unit and the base unit communicates the non indicia data messages with the optical reader;
wherein the optical reader display is configured to display non indicia data messages originating from the server; and,
wherein the HCS network is configured so that the hand held indicia reader and the base unit have a linking mode wherein a request to link is sent from the optical reader to the server through the base unit by way of wireless communication to associate the optical reader with the server.

12. A method of operating a health care service (HCS) network according to claim 11, wherein the non indicia data messages comprise at least one of the following:
text messages; audio messages; audio alerts; vibratory alerts; and images.

13. A method of operating a health care service (HCS) network according to claim 11, wherein the non indicia data messages have a unique identifier for receiving only by the optical reader.

14. A method of operating a health care service (HCS) network according to claim 11, wherein the linking mode comprises linking when the optical reader is placed in the base unit.

15. A method of operating a health care service (HCS) network according to claim 11, wherein the linking mode comprises linking by the optical reader decoding an indicia located on the base unit.

16. A method of operating a health care service (HCS) network according claim 11, wherein the display capability is limited to 150 characters of 6 point font.

17. A method of operating a health care service (HCS) network according claim 11, wherein the target is located at a patient point of care.

18. A method of operating a health care service (HCS) network according claim 11, wherein the optical reader is capable of reading biometric data.

19. A method of operating a health care service (HCS) network according claim 11, wherein at least one of the indicia data message and non indicia data message are encrypted.

20. A method of operating a health care service (HCS) network according claim 11, wherein at least one of the indicia data message and non indicia data message are encrypted according to a FIPS140 standard.

* * * * *